US005165927A

United States Patent [19]

Kaslow

[11] Patent Number: 5,165,927

[45] **Date of Patent: * Nov. 24, 1992**

[54] COMPOSITION WITH MODIFIED PERTUSSIS TOXIN

[75] Inventor: Harvey R. Kaslow, Los Angeles, Calif.

[73] Assignee: University of Southern California, Los Angeles, Calif.

[ * ] Notice: The portion of the term of this patent subsequent to Jul. 6, 2008 has been disclaimed.

[21] Appl. No.: 682,773

[22] Filed: Apr. 9, 1991

Related U.S. Application Data

[63] Continuation of Ser. No. 893,080, Aug. 1, 1986, Pat. No. 5,032,398.

[51] Int. Cl.[5] .............................................. A61K 39/10

[52] U.S. Cl. ...................................... 424/92; 530/403; 530/404; 530/406

[58] Field of Search ................... 424/92, 88; 574/2, 8, 574/21; 530/350, 351, 395, 402, 403, 404, 408, 825

[56] References Cited

U.S. PATENT DOCUMENTS

| | | | |
|---|---|---|---|
| 4,455,297 | 6/1984 | Syukuda et al. | 424/92 |
| 4,551,429 | 11/1985 | Greenspan | 435/68 |
| 4,687,738 | 8/1987 | Ginnaga et al. | 435/68 |
| 4,699,786 | 10/1987 | Lin et al. | 424/92 |
| 4,705,686 | 11/1987 | Scott et al. | 424/92 |
| 4,762,710 | 8/1988 | Sekura | 424/92 |
| 4,774,086 | 9/1988 | Quentin-Millet et al. | 424/92 |
| 4,788,058 | 11/1988 | Parton et al. | 424/92 |
| 4,996,299 | 2/1991 | Ginnaga et al. | 424/88 |
| 5,032,398 | 7/1991 | Kaslow | 530/351 |

FOREIGN PATENT DOCUMENTS

| | | |
|---|---|---|
| 19591 | 6/1976 | France . |
| 2083358 | 3/1982 | United Kingdom . |

OTHER PUBLICATIONS

AR–Katada et al., "The A Promoter of Islet–Activating Protein, Pertussis Toxin, as an Active Peptide Catalyzing ADP–Ribosylation of a Membrane Protein", *Archives of Biochemistry and Biophysics,* vol. 224, No. 1, Jul. 1, pp. 290–298, 1983.

AS–Sekura et al., "Pertussis Toxin", *The Journal of Biological Chemistry,* vol. 258, No. 23, Dec. 10, pp. 14647–14651, 1983.

AT–Tamura et al., "Subunit Structure of Islet-Activating Protein, Pertussis Toxin, in Conformity with A–B Model", *Journal of American Chemical Society,* vol. 21, No. 22, 1982, pp. 5516–5522.

AR[2]–Nogimori et al., "Chemical Modification of Islet–Activating Protein, Pertussis Toxin", *Biochimica et Biophysica Acta,* 801, (1984), pp. 220–231.

AS[2]–Carroll et al., "Photoaffinity Labeling of Diphtheria Toxin Fragment A with NAD: Structure of the Photoproduct at Position 148", *Proc. Natl. Acad. Sci. USA,* 82, Nov. 1985, pp. 7237–7241.

AT[2]–Leonard M. Hjelmeland, "A Nondenaturing Zwitterionic Detergent for Membrane Biochemistry: Design and Synthesis", *Proc. Natl. Acad. Sci. USA,* 77, No. 11, Nov. 1980, pp. 6368–6370.

AR[3]–Means et al., "Chemical Modification of Proteins", Holden–Day, Inc. 1971, pp. 11–15, 19, 105–113, 149–159, 171.

AS[3]–Lundblad et al., "Chemical Reagents for Protein Modification", vol. 1, CRC Press, Inc., Boca Raton, Fla., 1984, pp. 55–73 and 95–98.

AT[3]–Duncan et al., "Chemical Inactivation of Pertussis Toxin", 1986 ASM Annual Meeting, Official Abstract, Mar. 23–28, 1986.

AR[4]–Moss et al., *Biochemistry,* 25, 2720–5, 1986 (May 1986).

*Primary Examiner*—Merrell C. Cashion, Jr.
*Assistant Examiner*—Andrew G. Rozycki
*Attorney, Agent, or Firm*—Robbins, Dalgarn, Berliner & Carson

[57] ABSTRACT

A modified pertussis toxin suitable as a pertussis vaccine having an essentially unmodified B-oligomer and a catalytic subunit which is inactivated by treatment with polyphosphate compounds, sulfhydryl reductants and mild detergents followed by modification of the activated —SH groups to inhibit ADP-ribosylating activity.

3 Claims, 2 Drawing Sheets

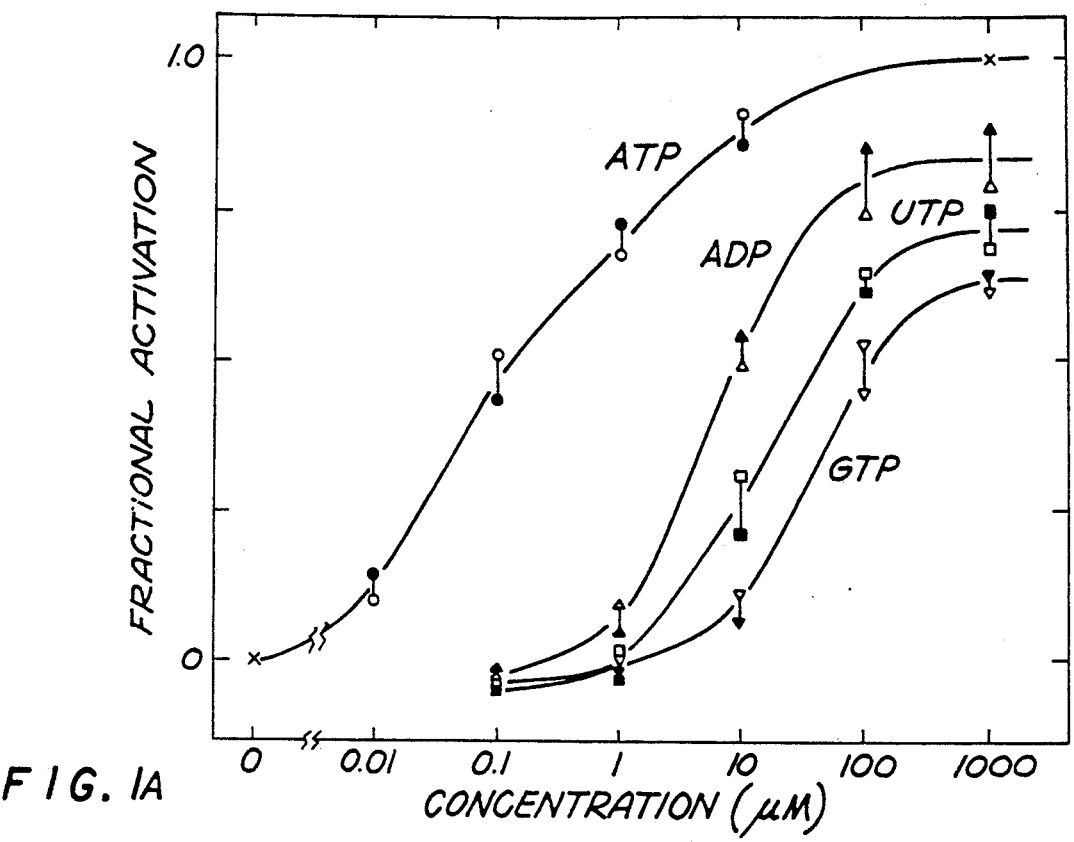
FIG. IA
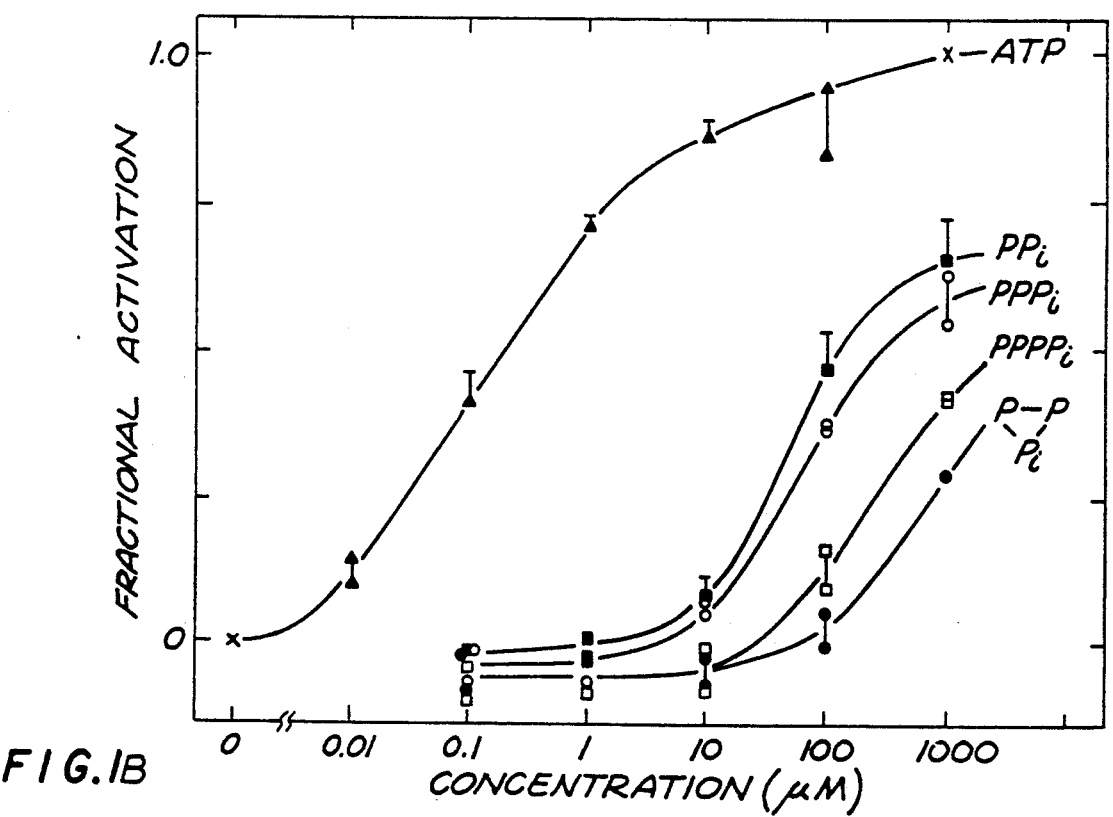
FIG. IB

COMPOSITION WITH MODIFIED PERTUSSIS TOXIN

The U.S. Government has rights to this invention under the terms of NIH Grant Number AM-31116.

This is a continuation of Ser. No. 06/893,080 filed Aug. 1, 1986, now U.S. Pat. No. 5,032,398.

FIELD OF THE INVENTION

This invention relates generally to the fields of chemistry and the medical sciences, and more particularly to biochemistry and the inactivation of toxins for the production of vaccines.

BACKGROUND OF THE INVENTION

The bacterium *Bordetella pertussis* elaborates a toxin (pertussis toxin) which produces symptoms of whoop pertussis, generally known as whooping cough. In the U.S., this disease affected over 200,000 children a year prior to the initial development of a whole-cell pertussis vaccine, killing as many as 12,000 per year. Since the introduction of this whole-cell vaccine, consisting of formalin- and/or heat-treated *B. pertussis*, the incidence of the disease has declined dramatically. However, the whole-cell vaccine can cause severe adverse reactions, including occasional permanent neurological damage.

In order to minimize such adverse reactions, an acellular vaccine has been developed containing purified pertussis toxin treated with formalin. Studies have indicated that for either the whole-cell or the acellular vaccine the attack rate, that is, the percent of children exposed to the disease who actually develop symptoms is from 10 to 15% while the attack rate in non-immunized children is 83%. Thus, both vaccines provide similar inadequate protection. The variable protection afforded by existing vaccines suggests either variable characteristics of, or responses to, the immunizing material and may be due to the fact that the effect of traditional techniques previously used for the inactivation of pertussis toxin are uncertain. For example, the toxin may be temporarily inactivated by heat or formalin treatment, only to have the denatured portions restructure to form either active or modified toxins which produce pertussis symptoms or neurologic damage.

Pertussis toxin is an oligomeric protein consisting of an A-protomer, containing an enzymatically active (catalytic) subunit, referred to as the $S_1$ subunit; linked to a B-oligomer which consists of one $S_2$, one $S_3$, two $S_4$ and one $S_5$ subunits. The B-oligomer binds to target cells, delivering the $S_1$ subunit which then produces symptoms of pertussis by ADP-ribosylating specific guanine-nucleotide-binding proteins and disrupting cellular functions.

SUMMARY OF THE INVENTION

The present invention provides for a gentle and selective modification of the pertussis toxin deactivating key amino acids in the catalytic portion of the toxin, yet leaving the antigenic determinants on the B-oligomer essentially undisturbed. The invention comprises a stable, modified pertussis toxin having an alkylated $S_1$ or catalytic subunit and an essentially unmodified B-oligomer, which is produced by the activation of the $S_1$ subunit followed by the alkylation of the revealed —SH groups, of that subunit, to selectively modify the toxin to produce a composition capable of inducing immunity to pertussis. The method produces a pertussis toxin which is selectively inactivated, that is, the ADP-ribosylating activity of the $S_1$ subunit is inactivated, as detected by NAD-glycohydrolase activity, yet the epitomatic characteristics of the B-oligomer are not modified. As used herein, an essentially unmodified B-oligomer refers to an oligomer which retains the epitomatic characteristics of pertussis toxin.

A variety of activating agents may be employed to prepare disulfide bonds of the protein chain of the $S_1$ subunit for subsequent deactivation by alkylation. While a specific range of NAD-glycohydrolase (NADase) activity is reported in the Examples hereinafter set forth, it should be understood that the percentage of activation-deactivation can easily be increased or decreased by variations in the time, temperature or concentration of the described activation and inactivation incubations. In order to limit the effects on the disulfide bonds of the B-oligomer, mild solutions and conditions are employed for this purpose.

Preferably, activating agents which aid in breaking the disulfide bonds of the $S_1$ subunit of pertussis toxin, and thus prepare the toxin for subsequent deactivation by alkylation, are selected from the groups consisting of solutions of polyphosphate compounds, sulfhydryl reductants and activators having lipophilic characteristics such as mild detergents. These classes of compounds act, respectively, on binding sites of the $S_1$ subunit which are referred to as the polyphosphate-site (P-site), the lipid-site (L-site), and the sulfhydryl-site (S-site). The P-site has been found to be a subsite, along with a receptor referred to as the adenosine-site (A-site), of the ATP binding site.

The members of the polyphosphate group may be selected from inorganic polyphosphates and multiphosphonucleotides. More specifically, polyphosphate, ATP, ADP and pyrophosphate are effective in activating the toxin. As used herein, the term activating when used with respect to the $S_1$ subunit relates to the reduction of the disulfide bonds in that subunit. In this regard, adenosine, inorganic phosphate, glucose-6-P (glucose 6-phosphate, a glucose metabolite) and amino acid monophosphates were ineffective for this purpose.

Compounds which act on the L-site of the $S_1$ subunit include the detergents cholic acid, 3-[(3-cholamidopropyl)-dimethylammonio]-1-propane sulfonate(CHAPS),3-[(3-cholamidopropyl)-dimethylammonio] 2-hydroxyl-1-propane sulfonate(CHAPSO), and polyethylene glycol non-ionic surfactants, especially polyoxythylene p-t-octylphenols (sold under the trade names Triton X-100 by Bio-Rad and NP-40 by Calbiochem), and octaethyleneglycol dodecyl ether.

The sulfhydryl reductants may be selected from the group including dithiothreitol (DTT), glutathione, cysteine and sodium borohydride. Sulfhydryl reductants having a reactive thiol group are particularly effective. The protein modifying reagents, that is, the sulfhydryl reagents employed to deactivate the $S_1$ subunit, are reagents which will serve to modify the sulfhydryl groups of the $S_1$ subunit, including haloacetates, haloacetimides, and N-ethylmaleimide. The sulfhydryl reagents are employed in a concentration which is in excess of the equivalent concentration of free sulfhydryl reductant remaining after the activation reaction, although higher concentrations may be employed up to a concentration where the B-oligomer is denatured solely as a result of this excess amount. Equivalent concentration is meant to impart a consideration of the fact that some reagents have more than one reactive group (e.g., DTT has two reductive thiol groups) and thus the equivalent concentration is a multiple of the molarity of the reagent.

The reaction conditions for the activation and deactivation reactions of the present invention offer substantial latitude for the method for the production of pertussis vaccine. While optimal reaction conditions are set forth in the following Examples, beneficial results may be obtained under a wide range of reaction parameters. For example, activation of the toxin occurs within a few minutes at 37° C., and while lowering the temperature to 0° C. slows the process, the activation reaction continues. Increasing the temperature above 37° C. will not adversely affect the activation reactions, but temperatures in excess of about 50° C. will risk thermal denaturation of the protein with the probable loss of haptenic image. Since the increase in temperature above 37° C. does not produce any substantial beneficial increase in results or reaction rate, the reaction has not been studied at elevated temperatures. The rate of the reaction of the protein modification (alkylation) reagents studied is generally unaffected by temperature variations. For example, haloacetates such as iodoacetate are highly reactive and inactivate toxin within about fifteen minutes at 30° C. Lowering the temperature to 0°–4° C. made no substantial difference. While warmer temperatures will have no deleterious effect on this reaction, in view of the highly reactive nature of the activated disulfide bonds on the $S_1$ subunit higher temperatures are unnecessary. Nonetheless, reaction temperatures both for the activation and the deactivation of the pertussis toxin may be from 0° C. up to the temperature which denatures the desired antigenic sites on the toxin.

Generally, the expression of enzymatic activity by the pertussis toxin is optimal at about pH 8. The extent of carboxymethylation of the toxin by iodoacetate decreases somewhat when the pH is lowered from 8 to 7, although the activation and deactivation reactions are not particularly sensitive to pH changes within the range dictated by chemical denaturation of the B-oligomer, and thus the pH of both reactions should be maintained at a pH of from about 6 to 10.

The polyphosphate activators should be used in a concentration of at least 1μM to fully activate the toxin. Preferably, concentrations of about 1 mM are used in the exemplars hereinafter set forth, although concentrations up to 100 mM may be employed especially with compounds such as ADP, GTP and pyrophosphates which have higher activation constants. It should be understood that concentration, especially as used with respect to the polyphosphate and sulfhydryl reductants, is expressed as free concentration of these reagents in the solution over that which is bound to the toxin or other reactants.

Lipophilic substances form micelles in aqueous solutions. That is, a portion of the detergent is in a micellar form and the remainder is free in solution. As the concentration of a detergent increases in an aqueous solution, there is a maximum concentration that can be free, and the remainder is in the form of micelles. In the present reaction, the detergent is preferably in an amount of detergent which is above the critical micellar concentration (CMC) of the particular detergent, i.e., an amount of detergent that will allow micelles to form in the presence of the amount of toxin sought to be inactivated. While detergents may be used at lower than their CMC, problems may arise in controlling the actual free concentration of the detergent. Therefore it is preferable to use detergents in the range of the critical micellar concentration, for example, CHAPS and CHAPSO are used in a concentration of 1 weight percent to provide a mild detergent solution in the reactions hereinafter described.

The sulfhydryl reactants are preferably in a free concentration of from about 0.1 to 100 mM, although more active reductants such as DTT are effective at concentrations of less than 10 nM.

The sulfhydryl reactants are preferably in a free concentration of from about 0.1 to 100 mM, although more active reductants such as DTT are effective at concentrations or less than 10 mM.

In summary, the reaction conditions are seen to be limited primarily by the deleterious denautrng effects on the B-oligomer. For this reason, mild reaction condition are preferred. In order to optimize the deactivation of the $S_1$ subunit while maintaining reaction conditions which are least able to denature the remaining portion of the toxin, it is preferred that the reagents which affect the P-, L-, and S-sites (that is, the pyrophosphate, the detergent and the sulfhydryl reductant agents) be used in combination.

DETAILED DESCRIPTION

Figure 2:
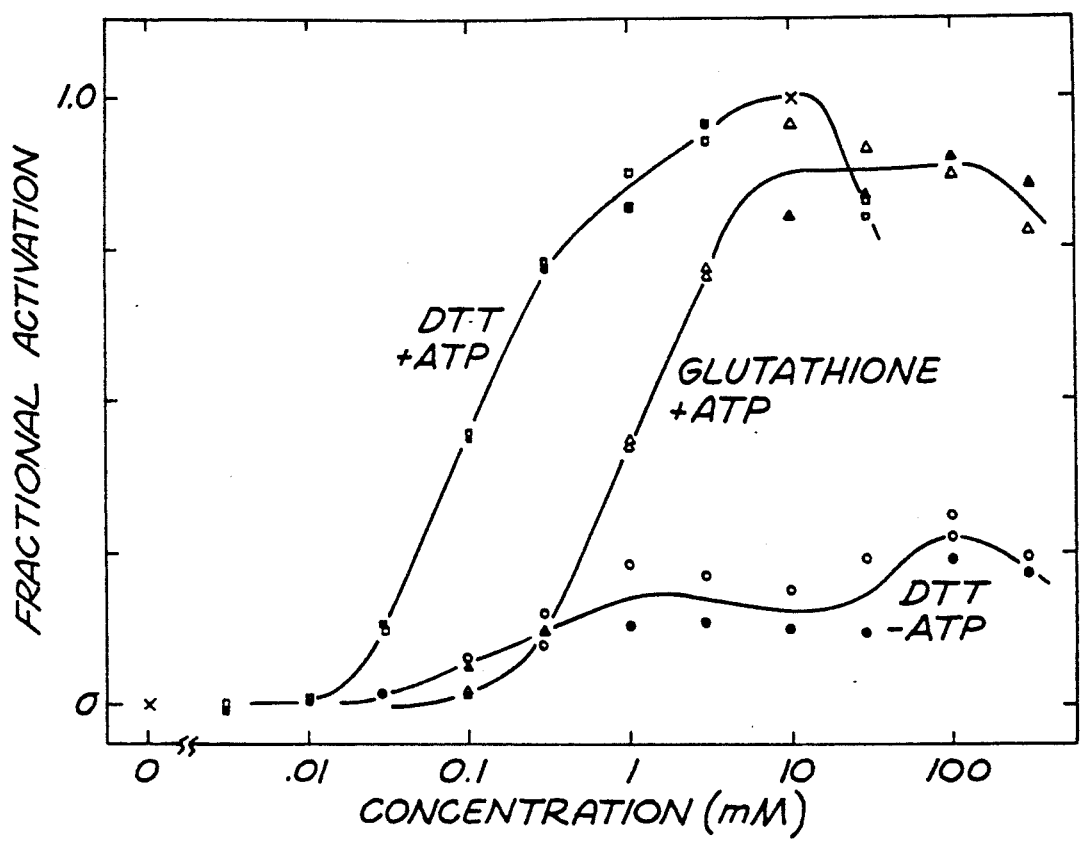

As set forth in the Examples, a deactivated pertussis toxin suitable for use as a vaccine is produced by the activation of the $S_1$ subunit of pertussis toxin with a preferred combination of specific polyphosphates, detergents and sulfhydryl reducing agents in order to prepare the toxin for the inactivation (i.e., inhibition) of the ADP-ribosylating activity by treatment with preferred protein-modifying reagents.

The ADP-ribosylating activity of the pertussis toxin can be detected as a nicotinamide-adenine dinucleotide-glycohydrolase (NADase) activity, which can be conveniently assayed through the use of [nicotinamide-$^{14}$C] or [nicotinamide-$^3$H] NAD. NAD consists of ADP-ribose linked to nicotinamide, and thus the extent of the release of ADP-ribose from NAD is an indication of the ability of the toxin to cause ill effects. In conducting this assay of the hydrolysis of labelled NAD, ion-exchange column chromatography was employed to resolve the produce from the substrate according to the method described by Moss et. al., *J. Biol. Chem.* 258, 11879 (1983) which is incorporated herein by reference. However, several modifications to this method were employed. First, a QAE-Sephadex resin was employed, as was a [nicotinamide-$^3$H] NAD. Specifically, a 2 ml QAE-Sephadex column was first washed with 10 ml 1NHCl, followed by 10 ml H$_2$O, 20 ml 0.5M Tris-HCl pH 7.0, and 40 ml H$_2$O. [$^3$H] NAD was applied, and the column washed with 20 ml water to elute impurities. Purified [$^3$H] NAD was eluted with 0.25M NaCl, and stored in small aliquots at −70° C. The purified [$^3$H] NAD contributed 50 mM NaCl (final concentration) to the NADase assays.

Before the end of the reaction, 2 ml QAE-Sephadex columns were treated with 10 ml 0.1M imidazole-HCl pH 7.0 with 1.0M NaCl, followed by 40 ml water. The NADase reaction (in 100μl) was terminated by adding 0.85 ml of ice-cold water, and the entire 0.95 ml was pipetted into a treated QAE column. The labelled nicotinamide was then eluted with 3 ml of water directly into a scintillation vial and counted. The absorbed labelled NAD was then eluted into radioactive waste with 10 ml 0.1M imidazole-HCl pH 7.0 with 1.0M NaCl, and the column stored partially immersed in a water bath until the next assay.

Preferably, the pertussis toxin is incubated at 30°–45° C. with the activating agents in a buffered solution at a pH of from about 6 to 10. For example, a Tris-HCl, sodium phosphate, sodium HEPES solution may be employed to advantage. The type of buffer is unimportant if the pH is effectively controlled and the buffer does not deleteriously react with the toxin or the alkylating reagents. The polyphosphate reagent is present in an amount of from about 0.5 to 5 mM, the non-denaturing detergent is present in a strength of from about 0.5 to 4 weight percent, and the sulfhydryl reductant is present in a molarity of from 0.5 to 10 mM. The time required for the initial activation of the pertussis toxin varies with concentration, but generally fifteen minutes to one hour at 37° C. has been sufficient. Following activation, an amount of the sulfhydryl reagent in slight excess of the amount of the reactive sulfhydryl reductant was added. In this regard, it should be noted that DTT has two reactive thiol groups. In order to detect the addition of the alkylatingsulfhydryl reagents, radioactive labelled reagents were employed.

In order to determine if any active toxin remained after the inactivation, a large excess of sulfhydryl reductant was added to each tube to scavenge unreacted sulfhydryl reagent. The NADase activity of the preparation was then measured. The three incubations were performed under a nitrogen atmosphere using degassed solutions to prevent oxidation of sulfhydryl groups which would prevent the sulfhydryl reagent from modifying the sulfhydryl group.

In the description herein, activation constants for the substances may be expressed by a numerical value ($A_{0.5}$) by using an NADase assay. This activation constant shows the potency of the substance in producing the enzymatic activity in the $S_1$ subunit and is expressed as the concentration needed for half of the maximum effect. For example, dithiothreitol (DTT) shows full activation at a concentration of 1 mM, yet requires only a concentration of 0.2 mM for half of this maximum effect.

The pertussis toxin in the Examples comprised 50μg of the toxin in a 500μl solution of 10 mM sodium phosphate-50 mM sodium chloride-water solution having a pH of 7. The enzymatic activity was detected as the hydrolysis of nicotinamide labelled NAD and ion-exchange column chromatography to resolve the product from the substrate. Unless otherwise noted, the assay was initiated by adding 0.5 to 2.5 μg of the toxin to a reaction mixture for a final volume of 100μl. The NADase reaction was terminated by adding 0.85ml of ice-cold water. The entire 0.95ml was then pipetted into a QAE-Sephadex column (chloride form) and the labelled nicotinamide eluted with 3ml of water directly into a scintillation vial and counted. NADase activity was linear with time up to three hours at 37° C. if 10% or less of the NAD was hydrolyzed. One unit of NADase activity is defined as 1 mol NAD hydrolyzed per hour.

EXAMPLE ONE

One-half microgram of pertussis toxin was incubated for thirty minutes at 370° C. in 100 mM Tris-HCl (pH 8.0), with or without activators, in a volume of 50μl. When present, ATP and pyrophosphate were present in a concentration of 2 mM, CHAPS at 2 weight percent, and DTT in a concentration of either 2 mM (trial 1) or 1 mM (trial 2). 10μl of water with or without iodoacetate or N-ethylmaleimide was then added and a second incubation conducted at 30° C. for either thirty minutes (trial 1) or fifteen minutes (trial 2). After this incubation, 10μl of 200 mM DTT was added to each tube, and the tubes were incubated for thirty (trial 1) or sixty minutes (trial 2) on ice to scavenge the iodoacetate or N-ethylmaleimide. ATP and CHAPS were then added to those tubes not containing them in order to express any latent activity, and water was added to equalize the volumes to 80μl. Each tube then received 20μl of labelled NAD, and was incubated at 37° C. for ninety minutes. The released nicotinamide was then isolated and counted as described above. During the NADase assay, the concentration of ATP was 1 mM, CHAPS was 1%, and DTT was 20-21 mM in all tubes. The first three incubations were done under a nitrogen atmosphere using degassed solutions, and the second incubation was done in the dark to avoid iodination of the protein. The NADase activity is shown in Table I and is expressed as the percent of the activity seen for the toxin treated in the same way without a deactivating alkylating agent. The numbers in parentheses indicate activity as a percent of the activity of pertussis toxin incubated on ice with only a buffer solution during the first three incubations. The NADase assay contained 125μM NAD in the first trial and 25μM NAD in the second, and the NADase activities of the toxins incubated on ice with the buffer, the iced controls, were 144 and 96 pmol per hour per microgram of toxin, respectively.

EXAMPLE TWO

Pertussis toxin (2.5μg) was incubated for thirty minutes at 37° C. in 50μl of 50 mM Tris-HCl (pH 8.0) with or without combinations of the activators ATP, CHAPS and DTT. During this incubation, ATP was mM, CHAPS was 1 weight percent, and DTT was 0.5 mM, when present. Following this incubation, 75 nmol (1.34 microCi of iodo[$^{14}$C] acetate and 25μl of water were then added, and the tubes incubated for an additional thirty minutes under nitrogen gas at 30° C. in the dark. This labelling reaction was terminated by adding 1 ml of ice-cold water containing 7.5 mM non-radioactive iodoacetate, 2.5μg bovine serum albumin, and 150μg sodium deoxycholate After ten minutes on ice, 100μl 72% triochloroacetic acid was added, and the precipitate recovered by centrifugation. Sodium dodecylsulfate and beta-mercaptoethanol were added, the sample heated to 95° C. for one minute, and then electrophoresed using 15% polyacrylamide gels. The fixed gels were then treated, dried and used to expose x-ray film at −70° C. Photographs of this film show the electrophoretic mobility of the various $S_1$–$S_5$ subunits of the toxin, and demonstrate that after activation of the toxin by DTT, ATP and CHAPS, iodoacetate carboxymethylated the enzymatic $S_1$ subunit.

EXAMPLE THREE

A wide variety of polyphosphates may be employed to activate pertussis toxin in the manner of the present invention. Under the conditions set forth in this Example, every di- and tri- phosphononucleotide and inorganic polyphosphate examined strongly stimulated the toxin. In contrast, adenosine, inorganic phosphate, glucose-6-P, and amino acid monophosphates were ineffective. Thus, the polyphosphate moiety, and not a nucleoside moiety, is required for stimulation of pertussis toxin.

The various compounds were screened for the ability to stimulate the NADase activity of the toxin when present in a concentration of 1 mM. Before assay the toxin (1μg per assay) was incubated at 37° C. for ten minutes with 20 mM DTT and 2 weight percent CHAPS. Assays were for three hours at 37° C., and fractional activation is defined as activity of the compound less the activity in the absence of an activator divided by the activity in the presence of 1 mM ATP less activity in the absence of the activator. The value given is the average plus one-half the range for two separate trials. In each trial, duplicates were measured. The NADase activity in units per microgram toxin in the absence of any ATP activation and in the presence of 1 mM ATP for the two trials was 44 and 111, and 18 and 97, respectively. The results are shown in Table II, wherein P denotes phosphate.

The activation constants ($A_{0.5}$) for several polyphosphates were determined in the presence of a mild detergent using the NADase assay, and these results are set forth in FIGS. 1A and 1B. Of all the tested compounds, ATP showed by far the lowest activation constant, approximately 200nM. The constants of the other substances were substantially greater under these conditions. The data in FIGS. 1A and 1B indicate the following activation constants in μM and (fraction of the ATP effect): ATP-0.2 (1.0), ADP-6 (0.8), UTP-15 (0.7) and GTP-35 (0.6). In addition, in FIG. 2B, data showing inorganic polyphosphates is shown, with PPi indicating pyrophosphate-45 (0.7), PPPi indicating tripolyphosphate-60 (0.6), PPPPi indicating tetrapolyphosphate at least 170 (0.4) and cyclic PPPi indicating trimetaphosphate at least 260 (0.3). It should be noted that the activation constants of GTP and tripolyphosphate are similar, indicating that the guanosine portion of GTP does little to either aid or interfere with activation. These results suggest that the adenosine portion of ATP appears to contribute to the effectiveness of this polyphosphate at low concentrations. However, adenosine failed to significantly alter the dose-response relationship of either ATP or pyrophosphate at concentrations of 1 mM, and thus there is no evidence to suggest that adenosine interacts with binding sites that stimulate the toxin.

EXAMPLE FOUR

As described above, mild detergents are preferred in the activation of pertussis toxin in the procedure described herein. The term mild, when used with respect to detergents, is meant to convey the meaning of a detergent which does not denature or modify the protein, and preferably have a concentration of less than about 3 percent b-y weight. The effect of detergents on the NADase activity of pertussis toxin was measured in the presence of various detergents at a concentration of 1 weight percent in either the absence or presence of the detergent CHAPS (1 percent by weight). ATP present in all in all assays in a concentration of 1 mM, and DTT concentration was 10 nM. Fractional activity is shown in Table III and is defined as activity divided by activity in the presence of 1% CHAPS. The value given is the average for two separate trials, and in each trial duplicates were measured for each condition. The results of the two trials differed by less than 4% of the activity in the presence of CHAPS alone, which in the two trials was 153 and 158 units per microgram.

EXAMPLE FIVE

A sulfhydryl reductant is used in combination with a mild cholic acid analog or non-ionic detergent, and a polyphosphate moiety to prepare the pertussis toxin for deactivation. Preferably, a sulfhydryl reductant having a reactive thiol group is preferred. In particular, DTT, glutathione and cysteine have been shown to be effective.

Pertussis toxin NADase activity was assayed in the presence of various sulfhydryl reducing agents at various concentrations. The assay buffer contained 1% CHAPS and 1 mM ATP. In FIG. 2, the NADase activities at various concentrations of glutathione are shown. Fractional activation is defined as activity less activity in the absence of reducing agent (which was essentially zero), divided by activity in the presence of 10 mM of the reducing agent less activity in the absence of the reducing agent. The NADase activities (U per microgram toxin) for 10 mM DTT without and with the presence of 1mM ATP were 18 and 147, 36 and 195, respectively. Cysteine was tested in a similar manner, and yielded essentially the same curve as did glutathione in FIG. 2. In the presence of ATP and CHAPS, glutathione activated pertussis toxin with an activation constant of 2mM. Cysteine activated with toxin with the same constant, showing that reagents commonly accepted as sulfhydryl reducing agents activate the toxin in the manner of the invention.

EXAMPLE SIX

Pertussis toxin was incubated first at 37° C. for fifteen minutes in 40 1 buffer A (100 mM Tris-HCl, pH 8.0 with 1 mM NaEDTA). EDTA was added to chelate divalent cations, which may promote oxidation of free —SH groups. During this incubation, DTT and ATP were present in concentrations of 1 mM each, and CHAPS was present in a concentration of 1 weight percent. Labelled iodoacetate was then added (10 1, 12.5 mM), and the tube incubated on ice for twenty hours. The sample was then mixed with sodium dodecylsulfate and β-mercaptoethanol, heated at 95° C. for one minute, and electrophoresed. After electrophoresis, the gel was fixed, treated with Fluorohance (Research Products International), dried and used to expose x-ray film. A scan of the x-ray film showed that the amount of label incorporated into the $S_1$ subunit is equal to the sum of that incorporated into the $S_2$ and $S_3$ subunits, and substantially more than the sum of that incorporated into the $S_5$ and $S_6$ subunits. If all of the cysteines on all subunits had reacted with the iodoacetate, the area of the doublet peak representing $S_2$ and $S_3$ should have been six times greater than that seen in $S_1$, the peak representing $S_4$ would have been two times greater, and that for $S_5$ also two times greater. Since the area under the peaks for these subunits is substantially less, the study demonstrates that a large fraction of the cysteines in the $S_2$-$S_5$ subunits did not react with the iodoacetate.

Further studies have demonstrated that including a detergent in the activation process has another important benefit. When CHAPS was added to the above-described reaction and compared with the addition of DTT and ATP or DTT alone, the peak indicating the alkylation of the $S_1$ subunit increases, and surprisingly the peaks indicating alkylation of the $S_2$ and $S_3$ subunits substantially decreases. This indicates that CHAPS stabilizes the B-oligomer of the toxin and allows it to resist denaturation of the disulfide bonds by sulfhydryl reductants, thus preserving the epitomatic structure of the toxin.

EXAMPLE SEVEN

Pertussis toxin was incubated at 37° C. for fifteen minutes as described in Example Six, and then a second incubation was begun by adding 10μl buffer A with or without 12.5 mM iodoacetate, mixing the contents of the tube and lowering the temperature to 30° C. After fifteen minutes, the tubes were shifted to an ice bath for ten minutes. A third incubation was then begun by adding 1μl buffer A containing 200 mM DTT to those tubes containing iodoacetate to scavenge the iodoacetate. To those tubes not containing iodoacetate during the second incubation, a mixture of 200 mM DTT and 12.5 mM iodoacetate in buffer A, previously incubated for an hour on ice, was added. The third incubation was continued for one hour on ice.

The contents of each tube were then assayed for NADase activity by adding 40μl of a reaction mix consisting of buffer A containing carbon-14 labelled NAD (final concentration in the 100μl final volume was 2μM), and 50 mM sodium chloride. Different reaction mixtures with various additions were used, so that in 37° C. for sixty minutes, and the released labelled nicotinimide isolated and counted. The iced controls were formed by incubating pertussis toxin (1μg) on ice in 10 mM sodium phosphate (pH 7) and 50 mM sodium chloride during the first three incubations. This toxin was then assayed for NADase activity under the same conditions and yielded a specific activity on the order of 100 picomols per hour per microgram of toxin. The first three incubations were done under a nitrogen atmosphere using degassed conditions, and the second and third incubations were done under subdued light. The results are shown in Table IV. From this Table, it can be seen that substantial advantages are provided by using all three classes of activators to prepare the toxin for inactivation with iodoacetate, and that the use of the adenosine polyphosphate and cholic acid analog detergent provides substantial advantages in the inactivation of NADase activity. It is also clear that CHAPS stabilizes the activity of toxin, consistent with the conclusion that is stabilizes the structure of the B-oligomer (See Example Six).

EXAMPLE EIGHT

The procedure followed in Example Seven was repeated for this study, except that N-ethylmaleimide, chloroacetamide or chloroacetate were substituted for iodacetate. After the 30° C. incubation, the tubes were either incubated for six minutes or eighteen hours at 0°-4° C. before the 10μl of 200 mM DTT (with or without quenched reagent) was added. Those tubes receiving the DTT after six minutes were incubated for nineteen hours at 0°-4° C. prior to the NADase assay. Those receiving the DTT after eighteen hours were incubated with DTT for one hour, as in Example Seven. The tubes were then assayed for NADase activity at the same time. The results are shown in Table V, wherein ND indicates a value which was not determined. It should be noted that the sulfhydryl reagents inactivate the toxin in expected rank order and time course. With respect to chloroacetate and chloroacetamide, it is thought that the inactivation can be improved under different conditions, as described above, particularly when the reaction is maintained at a higher pH.

From the foregoing description, it can be seen that the invention provides significant advantages, particularly when the preferred adenosine polyphosphate, reactive thiol sulfhydryl reductants, and cholic acid analog detergents are employed. Most preferably, the proven ATP, DTT and CHAPS reagents are employed.

Although the foregoing invention has been described in some detail by way of illustration and example, changes in form and substitution of equivalents are contemplated as circumstances may suggest or render expedient. Although specific terms have been employed herein, such terms are intended in a descriptive sense and not for purposes of limitation as the scope of the invention is delineated in the following claims.

TABLE I

| Additions to first incubation | Additions to second incubation | NADase activity (%) | |
|---|---|---|---|
| | | Experiment #1 | Experiment #2 |
| none | none | 100 (133) | 100 (73) |
| none | iodoacetate | 62 | 87 |
| none | N-ethylmaleimide | 90 | 106 |
| DTT, CHAPS, ATP | none | 100 (137) | 100 (93) |
| DTT, CHAPS, ATP | iodoacetate | 4 | 3 |
| DTT, CHAPS, ATP | N-ethylmaleimide | 11 | 13 |
| DTT, CHAPS, pyrophosphate | none | 100 (136) | 100 (117) |
| DTT, CHAPS, pyrophosphate | iodoacetate | 28 | 31 |
| DTT, CHAPS, pyrophosphate | N-ethylmaleimide | 60 | 46 |

TABLE II

| Compound | Fractional Activation: | Compound | Fractional Activation: | Compound: | Fractional Activation: |
|---|---|---|---|---|---|
| GTP | 0.87 + .01 | P | 0.01 + .01 | pyridoxal-P | 0.53 + .06 |
| CTP | 1.03 + .09 | pyro-P | 0.85 + .11 | glucose-6-P | −0.03 + .02 |
| UTP | 0.92 + .03 | tripoly-P | 0.98 + .14 | 2-glycerol-P | −0.01 + .03 |
| ITP | 0.85 + .01 | trimeta-P | 0.69 + .22 | serine-P | −0.04 + .02 |
| ADP | 1.07 + .06 | tetrapoly-P | 0.92 + .12 | threonine-P | 0.01 + .01 |
| AMP | 0.26 + .09 | thio-P | 0.12 + .06 | tyrosine-P | 0.02 + .02 |
| adenosine | 0.02 + .02 | | | | |

TABLE III

| Detergent | Fractional Activity | |
|---|---|---|
| | without CHAPS | with CHAPS |
| cholic acid analogs | | |

TABLE III-continued

| Detergent | Fractional Activity | |
|---|---|---|
| | without CHAPS | with CHAPS |
| none | 0.19 | 1 |
| CHAPSO | 1.05 | 1.04 |
| cholic acid | 0.43 | 1.02 |
| deoxycholic acid | 0.05 | 0.29 |
| *polyethylene glycol nonionic detergents* | | |
| NP-40 | 0.54 | 0.97 |
| Triton X-100 | 0.58 | 1.05 |
| $C_{12}E_8$ | 0.59 | 1.03 |
| *alkyl sulfobetaines* | | |
| Zwittergent-8 | 0.15 | 0.41 |
| Zwittergent-10 | 0.05 | 0.18 |
| Zwittergent-12 | 0.02 | 0.39 |
| Zwittergent-14 | 0.03 | 0.68 |
| *alkyl anionic detergents* | | |
| sodium dodecylsulfate | 0.02 | 0.03 |
| sodium lauryl sarcosine | 0.01 | 0.01 |

TABLE IV

| Additions to: | | Per cent NADase activity relative to: | |
|---|---|---|---|
| first incubation | second incubation | iced control | no addition to second incubation |
| none | none | 49 | 100 |
| none | iodoacetate | | 87 |
| DTT | none | 38 | 100 |
| DTT | iodoacetate | | 123 |
| ATP | none | 13 | 100 |
| ATP | iodoacetate | | 153 |
| ATP, DTT | none | 16 | 100 |
| ATP, DTT | iodoacetate | | 107 |
| CHAPS | none | 106 | 100 |
| CHAPS | iodoacetate | | 108 |
| DTT, CHAPS | none | 117 | 100 |
| DTT, CHAPS | iodoacetate | | 84 |
| ATP, CHAPS | none | 90 | 100 |
| ATP, CHAPS | iodoacetate | | 80 |
| ATP, DTT, CHAPS | none | 71 | 100 |
| ATP, DTT, CHAPS | iodoacetate | | 14 |

TABLE V

| Additions to: | | NADase activity as pmol per µg per hour and (per cent of activity with no addition to second incubation) length of second incubation: 15 minutes at 30° C. followed by: | |
|---|---|---|---|
| first incubation | second incubation | 6 minutes at 0–4° | 18 hours at 0–4° |
| none | none | ND | 51 (100) |
| none | iodoacetate | ND | 59 (116) |
| CHAPS | none | ND | 186 (100) |
| CHAPS | iodoacetate | ND | 171 (92) |
| DTT, CHAPS | none | ND | 191 (100) |
| DTT, CHAPS | iodoacetate | ND | 151 (79) |
| ATP, CHAPS | none | ND | 130 (100) |
| ATP, CHAPS | iodoacetate | ND | 110 (85) |
| ATP, DTT, CHAPS | none | 98 (100) | 103 (100) |
| ATP, DTT, CHAPS | iodoacetate | 17 (17) | 3 (3) |
| ATP, DTT, CHAPS | none | 109 (100) | 99 (100) |
| ATP, DTT, CHAPS | n-ethylmaleimide | 16 (15) | 10 (10) |
| ATP, DTT, CHAPS | none | 96 (100) | 98 (100) |
| ATP, DTT, CHAPS | chloroacetamide | 76 (79) | 35 (36) |
| ATP, DTT, CHAPS | none | 94 (100) | 98 (100) |
| ATP, DTT, CHAPS | chloroacetate | 86 (91) | 85 (87) |

What is claimed is:

1. A composition consisting essentially of a modified homogeneous pertussis toxin, wherein said modified pertussis toxin consists essentially of:
   a. the B-oligomeric component of the pertussis toxin in essentially unmodified form; and
   b. a modified catalytic subunit of pertussis toxin; in which at least one cysteine residue has been selectively modified so as to reduce ADP-ribosyltransferase activity; and has an ADP-ribosyltransferase activity which is reduced to no more than about 60% of the activity of the native toxin, wherein said ADP-ribosyltransferase activity is measured by comparison to the NAD-glycohydrolase activity possessed by the unmodified native catalytic subunit.

2. A pertussis toxin composition according to claim 1, wherein the catalytic subunit is essentially inactive.

3. A pertussis toxin composition according to claim 1, wherein said cysteine residue has been reduced and alkylated.

* * * * *

UNITED STATES PATENT AND TRADEMARK OFFICE
CERTIFICATE OF CORRECTION

PATENT NO. : 5,165,927

DATED : November 24, 1992

INVENTOR(S) : Harvey R. Kaslow

It is certified that error appears in the above-identified patent and that said Letters Patent is hereby corrected as shown below:

Col. 4, please delete lines 6 through 9.

Col. 4, line 15, please delete "denautrng" and substitute therefor --denaturing--.

Col. 7, line 55, please delete "b-y" and substitute therefor --by--.

Col. 7, line 59, after "ATP" and before "present", please insert --was--.

Col. 7, line 60, please delete the second occurrence of "in all".

Col. 7, line 61, please delete "10nM" and substitute therefor --10mM--.

Col. 9, line 12, please delete "1µl" and substitute therefor --10µl--.

Col. 9, line 23, delete "2µl" and substitute therefore --25µl--.

UNITED STATES PATENT AND TRADEMARK OFFICE
CERTIFICATE OF CORRECTION

PATENT NO. : 5,165,927

DATED : November 24, 1992

INVENTOR(S) : Harvey R. Kaslow

It is certified that error appears in the above-identified patent and that said Letters Patent is hereby corrected as shown below:

Col. 9, line 24, after "so that in" and before "37°", please insert --all tubes the final concentration of ATP was 1 mM and CHAPS was 1 weight percent. The assay was conducted at--.

Signed and Sealed this

Twenty-first Day of December, 1993

*Attest:*

BRUCE LEHMAN

*Attesting Officer*     *Commissioner of Patents and Trademarks*